United States Patent
Takeuchi et al.

(10) Patent No.: US 7,892,388 B2
(45) Date of Patent: Feb. 22, 2011

(54) PHOTOCURABLE RESIN COMPOSITION CONTAINING ANTHRAQUINONE DERIVATIVE

(75) Inventors: Fumito Takeuchi, Ichihara (JP); Yasushi Mizuta, Ichihara (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 373 days.

(21) Appl. No.: 12/159,130

(22) PCT Filed: Dec. 25, 2006

(86) PCT No.: PCT/JP2006/325798
§ 371 (c)(1), (2), (4) Date: Jun. 25, 2008

(87) PCT Pub. No.: WO2007/074782
PCT Pub. Date: Jul. 5, 2007

(65) Prior Publication Data
US 2009/0173438 A1    Jul. 9, 2009

(30) Foreign Application Priority Data
Dec. 27, 2005 (JP) .............. 2005-373640
Dec. 27, 2005 (JP) .............. 2005-373642

(51) Int. Cl.
*B32B 37/12* (2006.01)
*C08F 220/38* (2006.01)
*C09J 133/04* (2006.01)
*C07C 69/52* (2006.01)

(52) U.S. Cl. ............ 156/275.5; 526/273; 524/347; 524/853; 560/222

(58) Field of Classification Search ........... 156/275.5; 526/273; 524/347, 853; 560/222
See application file for complete search history.

(56) References Cited

U.S. PATENT DOCUMENTS

| 4,198,241 A | 4/1980 | Bronstert et al. |
| 7,566,377 B2 * | 7/2009 | Miyawaki et al. ...... 156/272.2 |
| 2006/0004140 A1 | 1/2006 | Asano et al. |
| 2006/0009579 A1 * | 1/2006 | Miyawaki et al. ...... 525/31 |

FOREIGN PATENT DOCUMENTS

| JP | 53-142490 A | 12/1978 |
| JP | 6-027662 A | 2/1994 |
| JP | 6-211758 A | 8/1994 |
| JP | 2003-313216 A | 11/2003 |
| JP | 2004-224993 A | 8/2004 |
| TW | I 232339 | 5/2005 |
| WO | WO 2004/041900 A1 | 5/2004 |

OTHER PUBLICATIONS

Office Action issued in corresponding Taiwanese patent application dated Jan. 26, 2010.
Form PCT/ISA/210 (International Search Report) dated Mar. 20, 2007.

* cited by examiner

Primary Examiner—Michael M Bernshteyn
(74) Attorney, Agent, or Firm—Buchanan Ingersoll & Rooney PC (57) ABSTRACT

Disclosed is a photocurable resin composition which is highly sensitive to ultraviolet light or visible light having a long wavelength, in particular a photocurable resin composition which is useful as a sealing agent. Specifically disclosed is a photocurable resin composition containing a component (a) which is composed of an anthraquinone derivative represented by the formula (I) below, and a component (b) which is composed of a compound having a (meth)acryloyl group in the molecule. The photocurable resin composition is characterized in that a part or the entire of the component (b) further contains an oxiranyl group in the molecule, and the component (a) content is 0.01-10% by mass relative to the component (b) content. [chemical formula 1] (I) (In the formula (I), X represents a phenyl group, an alkyl group having 1-8 carbon atoms, an alcoholic form of the phenyl group or the alkyl group, or a derivative of the alcoholic form.)

10 Claims, 1 Drawing Sheet

FIG.1

PHOTOCURABLE RESIN COMPOSITION CONTAINING ANTHRAQUINONE DERIVATIVE

TECHNICAL FIELD

The present invention relates to an anthraquinone derivative having a specific molecular structure and a photocurable resin composition containing the anthraquinone derivative.

BACKGROUND ART

A photocurable resin composition contains a component to be polymerized (for example, a monomer or an oligomer) and a photopolymerization initiator. The irradiating light for curing the photocurable resin composition is typically ultraviolet light and the like. The photocurable resin composition may be used as an adhesive, and is used for a wide application such as, for example, temporary stoppage of components to a print substrate, substrate masking, a main seal of a liquid crystal panel even in the field of electronic materials and record display materials.

As mentioned above, the photocurable resin composition may be used as an adhesive. In recent years, in the field of electronic materials and record display materials, the photocurable resin composition has been required to have high sensitivity, a low out-gas property and a high adhesion strength to a substrate. In addition, a photocurable resin composition, which is used as a sealing agent of a flat panel display including a liquid crystal display panel and an organic EL display panel, has been required to be cured by ultraviolet light in a relatively long wavelength region or visible light.

In the production of a liquid crystal display panel by the liquid crystal "one-drop-fill" (ODF) process, a liquid crystal is dropwise added to a substrate on which a sealing agent composed of a photocurable resin composition is applied and followed by light irradiating to cure the sealing agent. If the irradiating light is ultraviolet light of a short wavelength region, the liquid crystal molecules and the like are frequently damaged. For this reason, a special consideration has been required for light-shielding parts except for the desired irradiation part, narrowing the spot radius of a light source, and the like. Therefore, the photocurable resin composition for the sealing agent is strongly required to have a property to be cured by ultraviolet light in a relatively long wavelength region or visible light.

Furthermore, if a irradiating light for curing a photocurable resin composition is transmitted through an organic material substrate such as polycarbonate and the like, ultraviolet light having a short wavelength of less than 370 nm is absorbed by the substrate, thereby causing a problem that the resin composition was difficult to be sufficiently cured.

On the contrary, since ultraviolet light having a wavelength of 370 nm or more and visible light have a high transmissivity for an organic material substrate and there can be used any well-known lamp light source such as a high-pressure mercury lamp, a low-pressure mercury lamp, a metal halide lamp, a xenon lamp, a fluorescent lamp and the like, they are strongly required to be used as a wavelength for photocuring, from the viewpoint of environmental burden and energy saving.

In order to cure a photocurable resin composition by ultraviolet light in a relatively long wavelength region and visible light, it is important to suitably select a photopolymerization initiator. The conventional photopolymerization initiator is roughly classified into a self-cleavage type photoinitiator, a hydrogen-extraction type photoinitiator, and a photoinitiator using a light-induced electron transfer reaction.

The self-cleavage type photoinitiator is represented by an acetophenone derivative or the like, which absorbs light energy and is then cleaved to active radical species to initiate polymerization reaction. The hydrogen-extraction type photoinitiator is represented by benzophenone, thioxanthone and the like, which absorbs light energy and then generates active radical species by the hydrogen-extraction reaction of a carbonyl group to initiate polymerization reaction. The photoinitiator using a light-induced electron transfer reaction is represented by a combination of triazine and an organic dye, or a combination of an organized oxide and an organic dye, and the like.

Most of the photoinitiators contained in a common photocurable resin composition react with ultraviolet light. The photocurable resin composition containing such photoinitiators is not cured, or a sufficiently cured product may not be obtained without irradiating with the ultraviolet light having a relatively short wavelength of 300 nm or more and less than 370 nm.

On the one hand, as a photoinitiator reacting with a visible light, there is reported a photoinitiator which is a combination of thioxanthones, amines, camphorquinone, and the like (refer to Patent Document 1). The photoinitiator is not completely consumed by light irradiation and an unreacted photoinitiator remains. The unreacted photoinitiator may be eluted from the cured product or sublimated. In the food field where safety is emphasized and in the application of electronic components in which a small amount of impurities causes a problem, even if the generation amount of the photodegraded product is small, the unreacted photoinitiator may be transferred to the surface of the cured product to cause a problem. The malodor of amines may also cause a problem.

In addition, there has been developed a photocurable resin composition containing an α-aminoacetophenone-based or acylphosphine oxide-based photoinitiator, which is a self-cleavage type photopolymerization initiator having a light absorbance from ultraviolet light of a long wavelength region to visible light. However, since, for example, these photoinitiators generate, for example, benzaldehyde as a photodecomposed product, they could not be said to be a preferable photoinitiator from the viewpoint of reducing the amount of out-gas such as, for example, VOC (a volatile organic compound) and the like.

There has been proposed a photosensitizing agent having a (meth)acryloyl group at a part of a tetraalkyl-diamino-benzophenone skeleton (refer to Patent Document 2). However, the synthesis method is complicated, the radical generation efficiency is insufficient and the sensitivity is poor. There has been also proposed a thioxanthone derivative having an ethylenic unsaturated group (refer to Patent Document 3), but the electronic density of the aromatic ring is decreased because a carbonyl group is directly introduced into the thioxanthone as a substituent. For this reason, the radical generation ability is decreased and the sensitivity may be insufficient.

In addition, there has been reported a photopolymerizable substance, which contains a compound having a thioanthraquinone skeleton, for producing a relief printing block (refer to Patent Document 4).

[Patent Document 1] Japanese Patent Laid-Open Publication No. 2003-313216

[Patent Document 2] Japanese Patent Laid-Open Publication No. Hei 6-211758

[Patent Document 3] Japanese Patent Laid-Open Publication No. 2004-224993

[Patent Document 4] Japanese Patent Laid-Open Publication No. Sho 53-142490

DISCLOSURE OF THE INVENTION

Problems to be Solved by the Invention

As mentioned above, there are only a limited number of photocurable resin compositions that are highly sensitive to ultraviolet light in a relatively long wavelength region or visible light, and there has not been provided a photocurable resin composition having both a low out gas property and a property which is unlikely to impart a photodecomposed product.

The present invention provides these photocurable resin compositions by using a thioanthraquinone derivative having a specific structure. These photocurable resin compositions are preferably used as an adhesive or a sealing agent and the like in the electronic component field.

Means for Solving the Problems

In other words, the first of the present invention relates to a photocurable resin composition described below.

[1] A photocurable resin composition containing a component (a) composed of an anthraquinone derivative represented by the formula (I) and a component (b) composed of a compound having a (meth)acryloyl group in the molecule, wherein a part or the whole of the component (b) further has an oxiranyl group in the molecule and the content of the component (a) is 0.01 to 10% by mass relative to the content of the component (b).

(I)

wherein X represents a phenyl group or an alkyl group having 1 to 8 carbon atoms, an alcoholic form of the phenyl group or the alkyl group, or a derivative of the alcoholic form.

[2] The photocurable resin composition described in [1], wherein the component (a) contains a compound represented by the formula (I').

(I')

wherein $R_1$ is a hydrogen atom or a methyl group, Y is a phenylene group or its derivative, or an alkylene group having 1 to 8 carbon atoms or its derivative, Z is a single bond or a divalent organic group.

[3] The photocurable resin composition described in [1] or [2], wherein the composition further contains 10 to 50% by mass of a component (c) composed of a compound which contains an oxiranyl group in the molecule and has no radical polymerizability and 3 to 30% by mass of a latent epoxy curing agent (d), relative to the component (b).

[4] The photocurable resin composition described in [3], wherein the composition further contains 5 to 30 parts by mass of a filler (e), relative to 100 parts by mass of the photocurable resin composition.

[5] A sealing agent containing the photocurable resin composition described in any of [1] to [4].

[6] A liquid crystal sealing agent containing the photocurable resin composition described in any of [1] to [4].

[7] A sealing agent for the liquid crystal one drop fill process containing the photocurable resin composition described in any of [1] to [4].

The second of the present invention relates to a method of producing a liquid crystal panel described below.

[8] A method of producing a liquid crystal panel comprises a step of applying a sealing agent on a first substrate to form a desired frame shape; a step of dropwise supplying a liquid crystal in the frame of the frame shape; a step of overlapping the first substrate and a second substrate facing to the first substrate; and a step of curing the sealing agent by light, wherein the sealing agent contains the photocurable resin composition described in any of [1] to [4].

[9] A method of producing the liquid crystal panel described in [8] which further has a step of curing the sealing agent by heat.

[10] A method of producing the liquid crystal panel described in [8] or [9], wherein the light has a wavelength of 370 nm to 450 nm.

The third of the present invention relates to an anthraquinone derivative described below.

[11] An anthraquinone derivative represented by the following formula (I").

(I")

wherein one or more of $A_1$ to $A_8$ is or are a thioether group represented by the following formula (A), and $A_1$ to $A_8$ except for the thioether group represented by the formula (A) is or are a hydrogen atom or an alkyl group having 1 to 3 carbon atoms.

(A)

wherein $R_1$ is a hydrogen atom or a methyl group, Y is a phenylene group or its derivative, or an alkylene group having 1 to 8 carbon atoms or its derivative, Z is a single bond or a divalent organic group.

[12] A photocurable resin composition containing the anthraquinone derivative described in [11].

[13] A photocurable resin composition containing the anthraquinone derivative described in [12] and a compound having a (meth)acryloyl group.

EFFECT OF THE INVENTION

Since the photocurable resin composition of the present invention has excellent sensitivity to ultraviolet light of a long wave length or visible light and generates less amount of out-gas and the like in curing, it is especially advantageously used in the field of electronic materials and record display materials. Above all, it is preferably used as a liquid crystal sealing agent for producing a liquid crystal panel by the liquid crystal one drop fill process.

BEST MODE FOR CARRYING OUT THE INVENTION

The photocurable resin composition of the present invention contains the component (a) composed of the anthraquinone derivative represented by the following formula (I) and the component (b) composed of the compound having a (meth)acryloyl group.

(I)

The Component (a)

The component (a) is composed of a compound represented by the formula (I). In the formula (I), it is preferred that X should be a phenyl group or an alkyl group having 1 to 8 carbon atoms, an alcoholic form of the phenyl group or the alkyl group, or a derivative of the alcoholic form.

Examples of the phenyl group, its alcoholic form or its derivative represented by X, include phenyl group, phenoxy group, methoxyphenyl group (including 3-methoxyphenyl group) and the like.

Examples of the alkyl group having 1 to 8 carbon atoms represented by X include methyl group, ethyl group, propyl group, butyl group, pentyl group, hexyl group, heptyl group, octyl group and the like. Examples of the alcoholic form of the alkyl group having 1 to 8 carbon atoms represented by X include hydroxymethyl group, hydroxyethyl group, hydroxypropyl group, hydroxybutyl group and the like.

The derivative of the alcoholic form of a phenyl group or an alkyl group having 1 to 8 carbon atoms is, for example, a derivative in which the hydroxyl group of the alcohol is bonded with an arbitrary group by ester bond, ether bond or urethane bond. The arbitrary group bonded here preferably has a reactive functional group, and the reactive functional group includes a photopolymerizable functional group or a heat polymerizable functional group. An example of the photopolymerizable functional group includes a (meth)acryloyl group and an example of the heat polymerizable functional group includes an oxiranyl group.

In the case the compound represented by the formula (I) which is contained in the photocurable resin composition has a hydroxyl or a reactive functional group, when the photocurable resin composition is cured, the compound represented by the formula (I) may form a chemical bond with another component (for example, a monomer component) by hydrogen bonding, addition bonding and the like, thereby making it possible to suppress the elution of the compound represented by the formula (I) or its decomposed product.

Specific examples of the compound represented by the formula (I) include 2-phenylthio-9,10-anthraquinone; 2-(3-methoxyphenylthio)-9,10-anthraquinone; 2-(2-hydroxyethylthio)-9,10-anthraquinone; and derivatives of 2-(2-hydroxyethylthio)-9,10-anthraquinone, and the like.

The compound represented by the formula (I) may be produced by an arbitrary method and, for example, it may be produced with reference to the contents described in Japanese Patent Laid-Open Publication No. 2003-104930. In other words, it may be produced by reacting a compound having a thiol group with a halogenated hydroquinone (for example, 2-chloroanthraquinone).

The component (a) contained in the photocurable resin composition of the present invention may contain the compound represented by the formula (I'), which is one embodiment of an anthraquinone derivative represented by the formula (I). The compound represented by the formula (I') has a thioether group having a (meth)acryloyl group.

In the formula (I'), $R_1$ is a hydrogen atom or a methyl group. Y is a phenylene group or its derivative, or an alkylene group having 1 to 8 carbon atoms or its derivative. Z is a single bond or a divalent organic group. The divalent organic group is not particularly limited and may be selected accordingly depending on the production method of the compound.

The compound represented by the formula (I') may be produced by an arbitrary method and, for example, it may be produced through the following intermediate (II). Y is, as mentioned above, a phenylene group or its derivative, or an alkylene group having 1 to 8 carbon atoms or its derivative. "Halo" is a halogen atom such as chlorine. The intermediate (II) is produced with reference to the reaction of a halogenated anthraquinone with a hydroxyl group, which is described in Japanese Patent Laid-Open Publication No. 2003-104930.

"HS—Y—OH" in the above formula preferably is a mercaptophenol or an alkylalcohol having 1 to 8 carbon atoms which has a mercapto group.

The mercaptophenol may be any of para, meta or ortho. Further, examples of the alkylalcohol having 1 to 8 carbon atoms which has a mercapto group, include 2-mercaptoethanol, 1-mercapto-2-propanol, 3-mercapto-1-propanol, 4-mercapto-1-butanol, 3-mercapto-2-butanol, 5-mercapto-1-pentanol, 6-mercapto-1-hexanol, 3-mercapto-1-hexanol and the like. From the viewpoint of raw material availability, 2-mercaptoethanol, 1-mercapto-2-propanol and 3-mercapto-1-propanol are preferred.

The compound represented by the formula (I') may be produced; by subjecting the intermediate represented by the formula (II) to dehydration condensation reaction with (meth)acrylic acid; by subjecting the intermediate represented by the formula (II) to dehydration condensation reaction with carboxyl group of a (meth)acrylate having a carboxyl group; by subjecting the intermediate represented by the formula (II) to ring-opening addition reaction with an alkylene oxide and then subjecting the resulting hydroxyl group and a carboxyl group of a (meth)acrylate having a carboxyl group to dehydration condensation reaction; by subjecting the intermediate represented by the formula (II) to ring-opening addition reaction with an oxiranyl group of a (meth)acrylate having an oxiranyl group; by subjecting the intermediate represented by the formula (II) to urethanization reaction with an isocyanate group of a (meth)acrylate having an isocyanate group; or by reacting intermediate represented by the formula (II) with one isocyanate of a diisocyanate compound to form urethane bond and then reacting the other isocyanate of the diisocyanate compound with a (meth)acrylate having a hydroxyl group, but the production method is not particularly limited.

Hereinafter, a production example of the compound represented by the formula (I') is explained with reference to a chemical reaction formula.

The above-mentioned reaction formula is an example in which the intermediate (II) is subjected to dehydration condensation with (meth)acrylic acid. In this case, Z is a single bond.

The above-mentioned reaction is an example in which the intermediate (II) is subjected to dehydration condensation with an (meth)acrylate having a carboxyl group. In this case, Z is a carbonyloxy group.

Examples of the (meth)acrylate having a carboxyl group include caprolactone-modified (meth)acrylate, 2-(meth)acryloyloxyethyl phthalic acid, 2-(meth)acryloyloxyethyl succinic acid, 2-(meth)acryloyloxyethyl hydrophthalic acid, 2-(meth)acryloyloxyethyl maleic acid, 2-(meth)acryloyloxypropyl phthalic acid, 2-(meth)acryloyloxypropyl succinic acid, 2-(meth)acryloyloxypropyl maleic acid, and the like.

The above-mentioned reaction is an example in which the intermediate (II) is subjected to ring-opening addition reaction with an alkylene oxide and then to dehydration condensation with a (meth)acrylate having a carboxyl group. Examples of the alkylene oxide include ethylene oxide, propylene oxide, and the like. Examples of the (meth)acrylate having a carboxyl group include same compounds as those mentioned above. In this case, Z is an oxide group containing a carboxylate. In the above-mentioned reaction, since Y contained in the intermediate (II) is unlikely to react when it is an alkylene group, Y is preferably a phenylene group.

The above-mentioned two reaction formulas are examples in which the intermediate (II) is subjected to ring-opening addition reaction with a (meth)acrylate having an oxiranyl group. Specifically, one is a reaction formula in which a glycidyl(meth)acrylate is reacted, and another is a reaction formula in which 4-hydroxybutyl (meth)acrylate glycidyl ether is reacted. Even in the above-mentioned reaction, since Y contained in the intermediate (II) is also unlikely to react when it is an alkylene group, Y is preferably a phenylene group. In this case, Z is an alkylene oxide group having a hydroxyl group.

-continued

The above-mentioned two chemical formulas are examples in which the intermediate (II) is subjected to urethanization reaction with a (meth)acrylate having an isocyanate group. Specifically, one is a reaction formula in which the intermediate (II) is reacted with 2-(meth)acryloyloxyethyl isocyanate, and another is a reaction formula in which the intermediate (II) is reacted with 1,1'-[bis(meth)acryloyloxymethyl] ethyl isocyanate. In this case, Z is a carbamoyloxy group.

-continued

The above-mentioned chemical formula is an example in which the intermediate (II) is reacted with one isocyanate of a diisocyanate compound to urethane bond and further the other isocyanate of the diisocyanate compound is reacted with a (meth)acrylate having a hydroxyl group. In this case, Z is a carbamoyloxy group.

Specific examples of the diisocyanate compounds include trilene diisocyanate, diphenylmethane diisocyanate, xylylene diisocyanate, hexamethylene diisocyanate, isophorone diisocyanate, bis(isocyanatemethyl)cyclohexane, naphthalene diisocyanate, norbornene diisocyanate, 1,6-diisocyanate-2,2,4-trimethylhexane, and the like.

The reactivity of two isocyanates of the diisocyanate compound is preferably different from each other from the viewpoint of reaction control. Accordingly, the trilene diisocyanate and the isophorone diisocyanate may be preferably used.

Specific examples of the (meth)acrylate having a hydroxyl group include hydroxyethyl(meth)acrylate, hydroxypropyl(meth)acrylate, hydroxybutyl(meth)acrylate, diethyleneglycol(meth)acrylate, dipropyleneglycol(meth)acrylate, polyethyleneglycol(meth)acrylate, polypropyleneglycol(meth)acrylate, bis[(meth)acryloxyethyl]hydroxyethyl isocyanurate, further an acrylate in which caprolactone is ring-opening added to the hydroxyl group thereof, and the like. In consideration of raw material availability, viscosity of the products and compatibility with a photocurable monomer, the hydroxyethyl(meth)acrylate, the hydroxypropyl(meth)acrylate and the hydroxybutyl(meth)acrylate are preferred.

The content of the compound represented by the component (a) contained in the photocurable resin composition is typically 0.01 to 10% by mass and preferably 0.1 to 5% by mass relative to a compound (b) described later. If the content is 0.01% by mass or more, the required curability may be obtained, and if the content is 10% by mass or less, the required adhesion strength of the cured product may be obtained.

The component (a) may act as a photopolymerization initiator. Further, the compound represented by the formula (I) or (I') constituting the component (a) has an absorption band in a longer wavelength range, as compared with an anthraquinone derivative which has been conventionally used as a photopolymerization initiator. Therefore, the photocurable resin composition containing the component (a) may be cured by light of a relatively long wavelength. These matters will be explained in detail later.

Furthermore, the photocurable resin composition of another embodiment of the present invention contains the anthraquinone derivative represented by the following formula (I").

The compound represented by the formula (I") has an anthraquinone skeleton, and in which one or two or more of $A_1$ to $A_8$ of the formula (I") is or are substituted with the thioether group represented by the formula (A). The thioether group represented by the formula (A) may be substituted with any of $A_1$ to $A_8$, and preferably is substituted with $A_2$ and more preferably with $A_2$ only. When two or more of $A_1$ to $A_8$ are substituted with the thioether groups represented by the formula (A), the structures of each of the thioether groups may be the same or different.

$A_1$ to $A_8$ which are not substituted with the thioether group represented by the formula (A) are a hydrogen atom or a lower alkyl group (for example, an alkyl group having 1 to 3 carbon atoms, preferably a methyl group).

In addition, $R_1$ in the formula (A) is a hydrogen atom or a methyl group. Y in the formula (A) is a phenylene group or its derivative, or an alkylene group having 1 to 8 carbon atoms or its derivative. Z in the formula (A) is a single bond or a divalent organic group.

The thioether group represented by formula (A) has one or more (meth)acryloyl groups and may have two or more (meth)acryloyl groups. A specific example of the thioether group represented by formula (A) includes a group same as the thioether group of the compound represented by the formula (I').

The compound represented by the formula (I") may be produced in the same manner as that of producing the compound represented by the above-mentioned formula (I').

In addition, a preferred example of the compound represented by the formula (I") includes the compound represented by the above-mentioned formula (I').

The compound represented by the formula (I") may be used in arbitrary applications, but is preferably used as a photopolymerization initiator. In that case, the polymerization monomer may be a monomer having an ethylenic unsaturated group, and there may be used a conventionally known (meth)acrylate monomer.

The Component (b)

The component (b) contained in the photocurable resin composition is composed of the compound having a (meth)acryloyl group in the molecule. The number of the (meth)acryloyl group per one molecule may be one or two or more. The (meth)acryloyl group means an acryloyl group or a methacryl group.

An example of the compound having one (meth)acryloyl group per one molecule includes a (meth)acrylic ester. Examples of the (meth)acrylic ester include methyl ester, ethyl ester, propyl ester, butyl ester, amyl ester, 2-ethylhexyl ester, octyl ester, nonyl ester, dodecyl ester, hexadecyl ester, octadecyl ester, cyclohexyl ester, benzyl ester, methoxyethyl ester, butoxyethyl ester, phenoxyethyl ester, nonyl phenoxy ethyl ester, tetrahydrofurfuryl ester, 2-hydroxyethyl ester, 2-hydroxypropyl ester, 3-chloro-2-hydroxypropyl ester, dimethylaminoethyl ester, diethylaminoethyl ester, nonylphenoxyethyl tetrahydrofurfuryl ester, caprolactone modified tetrahydrofurfuryl ester, isobornyl ester, dicyclopentanyl ester, dicyclopentenyl ester, dicyclopentenyloxyethyl ester and the like.

In addition, the component (b) may contain an oligomer of these compounds.

An example of the compound having two or more (meth)acryloyl groups includes a multifunctional (meth)acrylic ester.

Examples of the multifunctional (meth)acrylic ester include di(meth)acrylates of 1,3-butylene glycol, 1,4-butanediol, 1,5-pentanediol, 3-methyl-1,5-pentanediol, 1,6-hexanediol, neopentyl glycol, 1,8-octanediol, 1,9-nonanediol, tricyclodecane dimethanol, ethylene glycol, polyethylene glycol, propylene glycol, polypropylene glycol and the like; di(meth)acrylate of tris(2-hydroxyethyl)isocyanurate;
(meth)acrylates having an isocyanuric acid skeleton such as tris[(meth)acryloxyethyl]isocyanurate, caprolactone modified tris[(meth)acryloxyethyl]isocyanurate and the like;
trimethylolpropane tri(meth)acrylate or its oligomer;
poly(meth)acrylate of aliphatic polyols or EO derivatives thereof, or poly(meth)acrylate caprolactone-modified or alkyl-modified alcohol such as EO modified trimethylolpropane tri(meth)acrylate, caprolactone modified trimethylolpropane tri(meth)acrylate, ditrimethylolpropane poly(meth)acrylate, EO modified ditrimethylolpropane poly(meth)acrylate, caprolactone modified ditrimethylolpropane poly(meth)acrylate, pentaerythritol poly(meth)acrylate or its oligomer, EO modified pentaerythritol poly(meth)acrylate, caprolactone modified pentaerythritol poly(meth)acrylate, dipentaerythritol poly(meth)acrylate, EO modified dipentaerythritol poly(meth)acrylate, alkyl modified dipentaerythritol poly(meth)acrylate, caprolactone modified dipentaerythritol poly(meth)acrylate and the like;
a di(meth)acrylate of an alkylene oxide or caprolactone modified bisphenol such as di(meth)acrylate of EO modified bisphenol A, di(meth)acrylate of PO modified bisphenol A, (meth)acrylate of caprolactone modified bisphenol A, di(meth)acrylate of EO modified bisphenol F and the like.

In addition, examples of the multifunctional (meth)acrylic ester may include polyester poly(meth)acrylate, polyether poly(meth)acrylate and urethane poly(meth)acrylate, which have been conventionally known.

In addition, examples of the multifunctional (meth)acrylic ester may include polyester poly(meth)acrylate, polyether poly(meth)acrylate and urethane poly(meth)acrylate, which have been conventionally known.

The component (b) is composed of the compound having the (meth)acryloyl group in the molecule, and a part or the whole of the component (b) further preferably has an oxiranyl group in the molecule. One or two or more oxiranyl groups are contained in the molecule.

If a compound composed of the component (b) has not only a (meth)acryloyl group but also an oxiranyl group in the molecule, photocurability and heat-curability may be imparted to the photocurable resin composition containing the component (b), thereby making it possible to increase the curability and adhesiveness of the cured product, and thus it is useful as an adhesive and a sealing agent.

Example of the compound having a (meth)acryloyl group and an oxiranyl group in the molecule, include conventionally known compounds, and include, for example, glycidyl (meth)acrylate, partial (meth)acrylate in which (meth)acrylic acid is added to an epoxy resin, epoxy modified urethane (meth)acrylate in which a (meth)acrylate having a hydroxyl group and an oxirane compound are bonded with diisocyanate, and the like.

Further, examples of the compound having a (meth)acryloyl group and an oxiranyl group in the molecule include epoxy(meth)acrylates such as bisphenol A diglycidylether di(meth)acrylate, bisphenol F diglycidylether di(meth)acrylate, PO modified bisphenol A diglycidylether di(meth)acrylate, phthalic acid diglycidylether di(meth)acrylate, and the like. A preferred example includes a vinyl compound in which 0.2 to 0.8 equivalent amount of (meth)acrylic acid is added to bisphenol A diglycidylether.

The compound having a (meth)acryloyl group and an oxiranyl group in the molecule, which is contained in the component (b), may be one kind or a combination of two or more kinds thereof.

In addition, in the component (b), the content of the compounds having a (meth)acryloyl group and an oxiranyl group in the molecule is arbitrary and is not particularly limited, but preferably is 50% by mass or more relative to the whole of the component (b).

The compound contained in the component (b) preferably is a photocurable compound, and typically the (meth)acryloyl group is addition-polymerized. Since the oxiranyl group has excellent thermal polymerizability, when a part or the whole of the component (b) further has the oxiranyl group, photocurability as well as heat-curability may be imparted to a photocurable resin composition. Especially, since a cured product obtained by addition-polymerizing the oxiranyl group by heat is excellent in adhesiveness and the like, it is suitable as a sealing material.

The Component (c)

The photocurable resin composition may contain the component (c) which contains an oxiranyl group and is composed of a compound having no radical polymerizability. The compound having no radical polymerizability may be a compound having no radical polymerizable functional group. An example of the radical polymerizable functional group includes a (meth)acryloyl group.

Since the photocurable resin composition containing the component (c) may have not only the photocurability but also a thermosetting property, it may be photocured and thermally cured to obtain a cured product having a strong crosslinking structure, thereby making it possible to improve the adhesiveness, durability and heat resistance of the cured product and further to secure adhesion reliability under high temperature and high humidity. Especially, when an effort is made to obtain a stronger cured product by curing the above-mentioned photocurable resin composition by radical photopolymerization and by subsequently heating, the component (c) is preferably added. A cured product with less curing strain may be obtained through a two-stage curing process in which the component (a) and the component (b) are reacted by radical photopolymerization and the component (c) is polymerized in the subsequent heating process.

Furthermore, as will be mentioned later, the photocurable resin composition of the present invention is preferably subjected to radical photopolymerization with ultraviolet light in a relatively long wavelength region (370 nm or more) or visible light. In the case where the photocurable resin composition is radical photopolymerized by light of the long wavelength region, the resulting cured product may have a lower degree of curing because the energy of light is different, compared to the case where it is radical photopolymerized under the same conditions except for using normal ultraviolet light (having a wavelength of less than 370 nm). In such a case, if the component (c) has been added to the above-mentioned photocurable resin composition, it is preferable as a sealing agent because a strong cured product may be obtained by thermally curing in addition to the radical photopolymerization.

An example of the compound contained in radical photopolymerized includes a conventionally known epoxy resin. Examples of the conventionally known epoxy resin include an aromatic polyhydric glycidyl ether compound obtained by the reaction between epichlorohydrin and aromatic diols (represented by bisphenol A, bisphenol S, bisphenol F, bisphenol AD and the like) or these aromatic diols modified by ethylene glycol, propylene glycol and alkylene glycol;

a novolac-type polyhydric glycidyl ether compound obtained by the reaction of a novolac resin epichlorohydrin derived from formaldehyde with phenol or cresol;

a polyhydric glycidyl ether compound obtained by the reaction of polyphenols (represented by a polyalkenyl phenol or its copolymer and the like) with epichlorohydrin;

glycidyl ether compounds of a xylene-phenol resin; and the like.

In addition, the component (c) includes an epoxidized diene polymer such as epoxidized polybutadiene, epoxidized polyisoprene and the like; bis(2,3-epoxycyclopentyl)ether; modified epoxy resins such as an urethane-modified epoxy resin, a polysulfide-modified epoxy resin, a rubber-modified epoxy resin (modified with CTBN, ATBN and the like), a polyalkylene glycol type epoxy resin, an ether elastomer added bisphenol A type epoxy resin, a silicone rubber-modified epoxy resin, acryl-modified epoxy resin and the like, so long as the feature of the present invention is not impaired.

The content of the component (c) in the photocurable resin composition is preferably 10 to 50% by mass relative to the component (b) in order to increase the adhesiveness and maintain the required photocurability.

The Latent Epoxy Curing Agent (d)

The photopolymerizable resin composition may contain the latent epoxy curing agent (d). The latent epoxy curing agent is not reacted with an epoxy group at a temperature for storing the composition normally (typically, room temperature), but has an ability of curing the composition when light or heat is acted on the composition. As the latent epoxy curing agent, those well-known may be employed, and there may be preferably mentioned organic acid dihydrazide compounds, imidazole and its derivative, dicyandiamide, aromatic amine and the like, from the viewpoint of their capability of imparting blended products which are one-liquid type and have good viscosity stability. These may be used alone or in a combination thereof.

Among these, a preferred example of the latent epoxy curing agent includes an amine-based latent curing agent that has a softening point of 100° C. or higher as measured by a melting point or a ring-and-ball method. The active hydrogen of the amino of the amine-based latent curing agent causes a nucleophilic addition reaction to a (meth)acryloyl group or an oxiranyl group of the compound contained in the component (b) or the component (c), thus improving curability and crosslinking density and increasing adhesion strength, heat resistance, durability and high-temperature and high-humidity adhesion reliability.

Specific preferred example of the amine-based latent curing agent include dicyandiamides such as dicyandiamide (melting point: 209° C.) and the like; organic acid dihydrazides such as dihydrozide adipate (melting point: 181° C.), 1,3-bis(hydrazinocarboethyl)-5-isopropylhydantoin (melting point: 120° C.) and the like; imidazole derivatives such as 2,4-diamino-6-[2'-ethylimidazolyl-(1')]-ethyltriazine (melting point: 215° C. to 225° C.), 2-phenylimidazole (melting point: 137 to 147° C.), 2-phenyl-4-methylimidazole (melting point: 174 to 184° C.), 2-phenyl-4-methyl-5-hydroxymethylimidazole (melting point: 191 to 195° C.) and the like; and the like.

The content of the latent epoxy curing agent (d) contained in the photocurable resin composition is typically 3 to 30% by mass and preferably 5 to 10% by mass relative to the component (b). If the content is within this range, the adhesion reliability is obtained and the viscosity stability of the adhesive composition may be maintained.

A Filler (e)

A filler (e) may be contained in the photocurable resin composition. The filler (e) preferably is a typical filler which may be used in the electronic material field. Specific examples of the filler (e) include inorganic fillers such as calcium carbonate, magnesium carbonate, barium sulfate, magnesium sulfate, aluminum silicate, zirconium silicate, iron oxide, titanium oxide, aluminum oxide (alumina), zinc oxide, silicate dioxide, sodium titanate, kaolin, talc, asbestos powder, quartz powder, mica, glass fiber and the like; and well-known organic fillers such as methyl polymethacrylate, polystyrene, and copolymer in which a monomer composed thereof and a monomer copolymerizable with the monomer are copolymerized. These fillers may have been graft modified with epoxy resin, silane coupling agent and the like.

The content of the filler (e) in the photocurable resin composition is typically 5 to 30% by mass and preferably 10 to 20% by mass, relative to the whole of the photocurable resin composition. If the content is within this range, the application stability and dimension stability are improved and the high-temperature and high-humidity adhesion reliability is increased.

Optional Components

The photocurable resin composition may contain other optional components. An example of the optional components includes a silane coupling agent. Examples of the silane coupling agent include, but is not particularly limited to, for example, vinyltrimethoxysilane, γ-(meth)acryloxypropyltrimethoxysilane, γ-glycidoxypropyltrimethoxysilane, γ-glycidoxypropyltriethoxysilane, β-(3,4-epoxycyclohexyl)ethyltrimethoxysilane, γ-mercaptopropyltrimethoxysilane and γ-aminopropyltriethoxysilane. These silane coupling agents may be used alone or in combination of two or more kinds thereof. In addition, these silane coupling agents may have been oligomerized by the dehydration condensation with other silane compound, for example, tetramethoxysilane, tetraethoxysilane, methyltrimethoxysilane and phenyltrimethoxysilane.

The content of the silane coupling agent in the photocurable resin composition preferably is 0.01 to 5% by mass, relative to the component (b). If the content is 0.01 part by mass, the adhesiveness is sufficiently improved, and if the content is 5 parts by mass or less, the amount of out-gas generated when the resin is cured is minimized.

Further, as the other components, there may be contained other polymerization initiator, sensitizer or co-catalyst.

Examples of these include tertiary amine, thiol compound, hydroquinone, or phenol compound having a steric hindrance, polymerization inhibitor such as phenothiazine and the like, solvent, antioxidant, antifoaming agent, dye and the like, which are used according to the objective.

Production Method of the Photocurable Resin Composition

The photocurable resin composition may be produced by an arbitrary method so long as the effect of the present invention is not impaired, and may be obtained by mixing each of the above-mentioned components by a conventional method. In case of mixing the ingredients, there may be employed well-known kneading machines such as a double arm stirrer, a roll kneader, a biaxial extruder, a ball mill kneader and the like, and finally the resulting composition is filled and sealed in a glass bottle or a plastic container and then may be stored and transported.

Applications of the Photocurable Resin Composition

Since the photocurable resin composition of the present invention is cured by light irradiating, it is used for the same applications as a typical photocurable resin composition, but is preferably used as a sealing agent. In case of using as a sealing agent, the resin composition of the present invention is applied to the parts to be sealed and then is cured by light irradiating.

For the light irradiation, there may be employed a conventionally known light source for emitting ultraviolet light and visible light. In case of irradiating with visible light, there can be used any well-known lamp light source such as a high-pressure mercury lamp, a low-pressure mercury lamp, a metal halide lamp, a xenon lamp, a fluorescent lamp, and the like.

The light, irradiating for curing the photocurable resin composition of the present invention, may be visible light or ultraviolet light of a relatively long wavelength. The mechanism is not limited, but, for example, the anthraquinone derivative contained in the resin composition of the present invention is excited by absorbing the light, thereby inducing a hydrogen extraction reaction from a monomer.

The present inventor has found that the anthraquinone derivative represented by the formulas (I) and (I') and the compound represented by (I") absorb light of a longer wavelength band, as compared with the anthraquinone derivative which has been conventionally used as a photopolymerization initiator. As the reason for this, it is considered that a thioether group is bonded to the anthraquinone skeleton.

Figure 1:
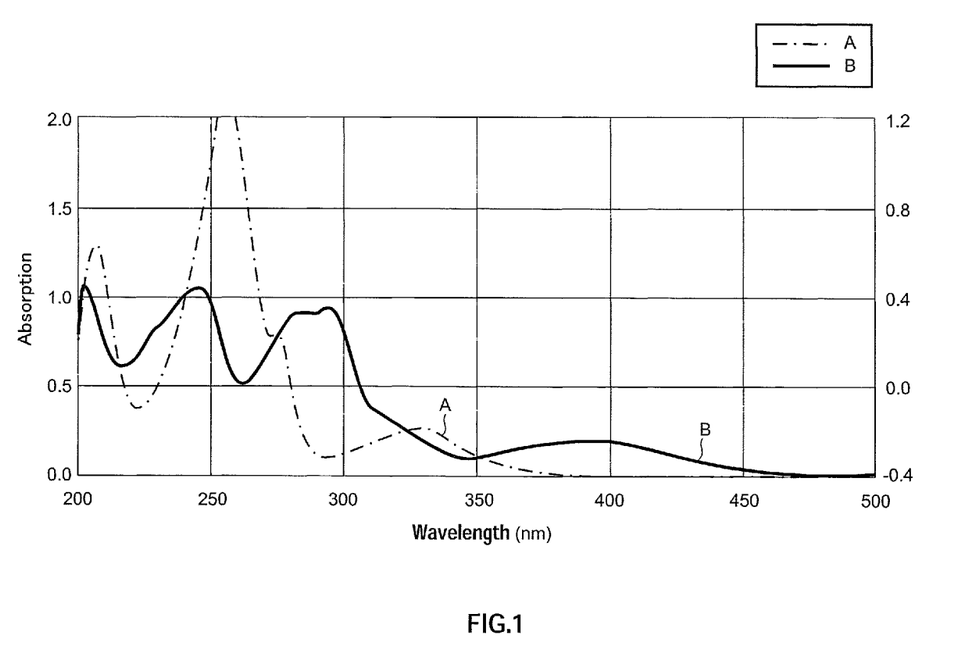
FIG. 1 A light absorption spectrum of a compound having an anthraquinone skeleton.

FIG. 1 is a light absorption spectrum of a compound represented by the following structural formula. As described in the following formula B, "a compound having an anthraquinone skeleton to which a thioether group is bonded" absorbs light of a longer wavelength band (approximately 400 nm) than "a compound having a anthraquinone skeleton to which a thioether group is not bonded" as described in the following formula A. In this way, the compounds represented by the formulas (I), (I') and (I") preferably have an absorption peak in the range of 370 to 450 nm.

A

-continued

B

The measurement of the light absorption was carried out by using a methanol solution ($1.5 \times 10^{-3}$% by weight) as a sample and an ultraviolet-visible spectrophotometer (UV-2550: manufactured by Shimadzu Corporation).

In this way, since the photocurable resin composition of the present invention is cured by irradiating with light of a relatively long wavelength, it is especially suitably used as a sealing agent for sealing a material which is easily deteriorated by light. For example, since a liquid crystal molecule tends to be deteriorated by light, the photocurable resin composition is preferably used as a liquid crystal sealing agent in the production of a cell of liquid crystal panel. The liquid crystal sealing agent preferably contains spacer particles and the like together with the photocurable resin composition of the present invention. The spacer particles are particles for providing a gap between the substrates (typically glass substrates) of a liquid crystal panel and are typically silica particles.

In recent years, with the increase in size of a screen of a liquid crystal panel, the production system of the cell has transferred from "a liquid crystal injection method" to "a liquid crystal one drop fill process". The liquid crystal one drop fill process typically comprises steps of: applying a sealing agent on a first substrate to form a desired frame shape; dropwise supplying a liquid crystal in the frame of the frame shape; overlapping the first substrate and a second substrate facing to the first substrate; curing the sealing agent by light; and further curing the sealing agent by heat where necessary.

In the step of curing the sealing agent by light in the "liquid crystal one drop fill process", if the liquid crystal added dropwise in the frame is also irradiated with light, the liquid crystal may be deteriorated. The deterioration of the liquid crystal may be suppressed by using the photocurable resin composition of the present invention as a sealing agent (a sealing agent for the liquid crystal one drop fill process) and curing by light of a relatively long wavelength (light having weak energy).

The light for curing the said sealing agent preferably has a wavelength of 370 to 450 nm. The reason is to cure the composition sufficiently and to suppress the deterioration of liquid crystal molecules and the like by light.

EXAMPLES

Hereinafter, the present invention will be explained in detail with reference to representative examples, but the present invention is not limited by these examples. "Parts" described in examples represents "parts by mass".

Example 1

Synthesis 1 of Anthraquinone Derivative

To a 500 ml four-necked flask equipped with a stirrer, a nitrogen gas introduction tube, a thermometer and a reflux cooling tube, 2-(2-hydroxyethylthio)-9,10-anthraquinone (Kawasaki Kasei Chemicals Ltd.)(10.0 g; 1 mol equivalent), Karenz BEI (8.9 g; 1 mol equivalent) and THF (100 mL) were added. The contents in the four-necked flask were uniformly dissolved at room temperature under nitrogen flow. Thereafter, dibutyltin dilaurate (0.02 g) was dropwise added and reacted at the same temperature for 3 hours.

After completion of the reaction, THF was removed using an evaporator under the condition at 50° C. and 8000 to 10000 Pa. To the residue toluene (500 mL) was added, and the mixture was uniformly dissolved and washed with ultrapure water 5 times. After washing, toluene was removed using the evaporator again under the condition at 50° C. and 8000 to 10000 Pa to obtain a yellow viscous liquid. It was confirmed by FT-IR and $^1$H-NMR that an acryloyl group was completely introduced (refer to the following $^1$H-NMR data). The resulting liquid was used in Examples 4 and 5 described below.

$^1$H-NMR (CDCl$_3$, ppm): δ 1.45 (s, 3H), 3.43 (t, 2H) 4.22-4.28 (m, 6H), 5.30 (s, 1H), 5.80-5.90 (m, 2H), 6.03-6.21 (m, 2H), 6.35-6.48 (d, 2H), 7.63-7.70 (d, 1H) 7.75-7.86 (m, 2H), 8.15-8.36 (m, 4H)

Example 2

Synthesis 2 of Anthraquinone Derivative

A 500 ml four-necked flask equipped with a stirrer, a nitrogen gas introduction tube, a thermometer and a reflux cooling tube, 2-(2-hydroxyphenylthio)-9,10-anthraquinone (Kawasaki Kasei Chemicals Ltd.)(10.0 g; 1 mol equivalent), glycidyl(meth)acrylate (4.8 g; 1 mol equivalent) and tetrabutylammonium bromide (0.5 g) and toluene (100 mL) were charged, and then reacted at 90° C. for 10 hours under nitrogen flow while bubbling with dry air.

After completion of the reaction, toluene (500 mL) was added and uniformly dissolved and then washed with ultrapure water (200 mL) 5 times. After washing, toluene was removed using the evaporator under the condition at 50° C. and 8000 to 10000 Pa. The resulting photopolymerization initiator was a yellow viscous liquid, and it was confirmed by FT-IR and $^1$H-NMR that an acryloyl group was completely introduced (refer to the following $^1$H-NMR data). The resulting liquid was used in Example 6 described below.

$^1$H-NMR (CDCl$_3$, ppm): δ 1.97 (s, 3H) 4.21-4.44 (m, 4H), 5.60 (s, 1H), 6.19 (m, 1H), 6.50-6.58 (d, 2H), 7.12-7.20 (d, 2H), 7.63-7.70 (d, 1H), 7.75-7.86 (m, 2H), 8.15-8.36 (m, 4H), 8.93 (s, 1H)

Example 3

Preparation 1 of Resin Composition

A mixture of the following respective components was heated and dissolved to form a uniform solution.
(a) Photopolymerization initiator: 1 part
  2-(2-hydroxyethylthio)-9,10-anthraquinone (produced by Kawasaki Kasei Chemicals Ltd.)
(a') Other photopolymerization initiator: 2 parts
  KIP 150 (poly[2-hydroxy-2-methyl-4-(1-methylvinyl) phenyl) propanone]: produced by Lamberti)
(b1) Compound having acryl group: 25 parts
  Trimethylolpropane EO-addition triacrylate (VISCOAT V#360, produced by Osaka Organic Chemical Industry Co., Ltd.)
(b2) Compound having acryl group: 59 parts
  Bisphenol A epoxy diacrylate (VISCOAT V#540, produced by Osaka Organic Chemical Industry Co., Ltd.)

To the resulting uniform solution the following respective components were added and premixed by a mixer.
(d1) Latent epoxy curing agent: 8 parts
  1,3-bis(hydrazinocarboethyl)-5-isopropylhydantoin (Amicure VDH-J; produced by Ajinomoto Co., Inc.)
(d2) Latent epoxy curing agent: 1 part
  2-phenyl-4-methylimodazole (Curezol 2P4MZ, produced by Shikoku Chemicals Corporation)
(e) Filler: 15 parts
  Ultra-high-purity silica (SO-E1: produced by Admatechs Co., Ltd.)
(f) Coupling agent: 1 part
  γ-glycidoxypropyltrimethoxysilane (KBM-403: produced by Shin-Etsu Chemical Co., Ltd.)

The resulting mixture was kneaded by a three-roll mill until the particle diameter of the solid raw materials ((d1), (d2) and (e)) becomes 5 μm or less, and the kneaded product was subjected to vacuum defoaming treatment to obtain a photocurable resin composition (P3).

Example 4

Preparation 2 of Resin Composition

A photocurable resin composition (P4) was obtained in the same manner as in Example 3 using the compound of Example 1 in place of 2-(2-hydroxyethylthio)-9,10-anthraquinone as the photopolymerization initiator.

Comparative Example 1

A photocurable resin composition (C1) was obtained in the same manner as in Example 3 using KIP 150 (poly[2-hydroxy-2-methyl-(4-(1-methylvinyl)phenyl)propanone]: produced by Lamberti) in place of 2-(2-hydroxyethylthio)-9,10-anthraquinone as the photopolymerization initiator.

Comparative Example 2

A photocurable resin composition (C2) was obtained in the same manner as in Example 3 using Lucirin TPO (2,4,6-trimethylbenzoyldiphenylphosphineoxide; produced by BASF Corporation) in place of 2-(2-hydroxyethylthio)-9,10-anthraquinone as the photopolymerization initiator.

Comparative Example 3

A photocurable resin composition (C3) was obtained in the same manner as in Example 3 using Speedcure DETX (2,4-diethylthioxantone: produced by LAMBSON Ltd.) in place of 2-(2-hydroxyethylthio)-9,10-anthraquinone as the photopolymerization initiator.

Example 5

Preparation 3 of Resin Composition

There were mixed the compound (1 part) of Example 1 as the photopolymerization initiator and bisphenol APO modified diglycidylether diacrylate (100 parts) (Epoxyester 3002M: Kyoeisha Chemical Co., Ltd.) in a separable flask and then the kneaded product was subjected to a vacuum defoaming treatment to obtain a photocurable resin composition (P5).

Example 6

Preparation 4 of Resin Composition

A photocurable resin composition (P6) was obtained in the same manner as in Example 5 using the compound of Example 2 in place of the compound of Example 1 as the photopolymerization initiator.

Comparative Example 4

A photocurable resin composition (C4) was obtained in the same manner as in Example 5 using KIP 150 (poly[2-hydroxy-2-methyl-(4-(1-methylvinyl)phenyl)propanone]: produced by Lamberti) in place of the compound of Example 1 as the photopolymerization initiator.

Comparative Example 5

A photocurable resin composition (C5) was obtained in the same manner as in Example 5 using Lucirin TPO (2,4,6-trimethylbenzoyldiphenylphosphineoxide; produced by BASF Corporation) in place of the compound of Example 1 as the photopolymerization initiator.

Comparative Example 6

A photocurable resin composition (C6) was obtained in the same manner as in Example 5 using Speedcure DETX (2,4-diethylthioxantone: produced by LAMBSON Ltd.) in place of the compound of Synthesis Example 1 as the photopolymerization initiator.

The following tests were carried out for the photocurability, the out-gas measurement and the elution amount of the photopolymerization initiator of the photocurable resin compositions (P3 to P6) obtained in Examples 3 to 6 and the photocurable resin compositions (C1 to C6) obtained in Comparative Examples 1 to 6. In addition, the following tests were carried out for the adhesion strength and the high-temperature and high-humidity adhesion reliability of P3 and P4 and C1 to C3.

The respective test results are shown in Table 1 (P3 and P4 and C1 to C3) and Table 2 (P5 and P6 and C4 to C6).

1. Photocurability Test

Each of the photocurable resin compositions was set to the measuring cone type (a diameter of 10 mm) of a UV rheometer (ViscoAnalyser 100: manufactured by REOLOGICA Instruments AB).

The light energy required for curing was measured by adjusting the light intensity at 405 nm to 3 mW/cm$^2$ and irradiating light (ultraviolet or visible) having a wavelength of 370 nm to 450 nm.

In the Tables 1 and 2, when the amount of light energy required for curing was 30 mJ/cm$^2$ or less the composition is marked with "○", when that was 30 to 100 mJ/cm$^2$ the composition is marked with "Δ", and when that was 100 mJ/cm$^2$ or more the composition is marked with "x"

2. Out-Gas Measurement Test in Photocuring

Each of the photocurable resin compositions (10 mg) was weighed and sealed in 10 mL of vial bottle. Light curing was carried out by irradiating with light (ultraviolet or visible) having a wavelength of 370 to 450 nm at an irradiation intensity of 100 mW/cm$^2$ and light energy of 2000 mJ/cm$^2$ through an ultraviolet light+heat ray cutting filter via the bottom surface of the vial bottle using an ultraviolet light irradiation apparatus manufactured by Toshiba Corporation. Thereafter, the head space (HP 7694: manufactured by Hewlett-Packard) was heated at 120° C. for 5 minutes the out-gas measurement was carried out by GC(HP-90: manufactured by Hewlett-Packard). The out-gas amount was measured in ppm in terms of toluene.

3. Elution Amount Test of Photopolymerization Initiator from Cured Product

Each of the photocurable resin compositions was applied on a Teflon (registered trademark) substrate using an applicator of 100 μm. Light curing was carried out by irradiating with light (ultraviolet or visible) having a wavelength of 370 to 450 nm at an irradiation intensity of 100 mW/cm$^2$ and light energy of 2000 mJ/cm$^2$ to the coated film through an ultraviolet light+heat ray cutting filter under nitrogen atmosphere. Thereafter, the resulting cured product was subjected to heat treatment at 120° C. for 60 minutes under nitrogen atmosphere in an oven to prepare a film-like adhesive cured product of 100 μm.

The prepared cured product (0.1 g) and methanol (10 g) were added into a round-bottom flask (100 mL of volume) and extraction was conducted in an oil bath at 80° C. for one hour, followed by quantitatively measuring the elution amount of the unreacted photopolymerization initiator by LC-MS (LCMS-2010, manufactured by Shimadzu Corporation). The elution amount was calculated in ppm based on the calibration curve prepared for each of the photopolymerization initiators.

4. Adhesion Strength Measurement Test

A photocurable resin composition, in which glass fibers of 5 μm were added (the addition amount: 1% by mass) as spacer particles, was screen printed in a circle shape having a diameter of 1 mm on a non-alkali glass having a length of 25 mm, a width of 45 mm and a thickness of 5 mm. A similar glass, which forms a counterpart of the non-alkali glass, was adhered crosswise. Light curing was carried out by irradiating with light (ultraviolet or visible) having a wavelength of 370 nm to 450 nm at an irradiation intensity of 100 mW/cm$^2$ and light energy of 2000 mJ/cm$^2$ through an ultraviolet light+heat ray cutting filter by using an ultraviolet light irradiation apparatus manufactured by Toshiba Corporation while applying load. Further, the resulting cured product was subjected to heat treatment at 120° C. for 60 minutes under nitrogen atmosphere in an oven.

The resulting test specimen was measured for a flat tensile strength at a strain rate of 2 mm/min using a tensile tester (Model 210: manufactured by Intesco Co., Ltd.).

5. Adhesion Reliability Test after High-Temperature and High-Humidity Acceleration Test.

A test specimen was prepared in the same manner as in adhesion strength measurement test 4. The resulting adhesion test specimen was stored in a high-temperature and high humidity acceleration tester at a temperature of 121° C., a humidity of 100% and a pressure of 2.1 atmospheric pressure for a pressure cocker tester (ETAC PLAMOUNT PM422: manufactured by Kusumoto Chemicals Ltd.). The test specimen after storing 20 hours was measured for the flat tensile strength at a strain rate of 2 mm/min using the tensile tester (Model 210: manufactured by Intesco Co., Ltd.).

In table 1, test specimens having more than 50% of the adhesion strength retention to the adhesion strength before the high-temperature and high humidity acceleration test were marked with "○", test specimens having 30 to 50% of that were marked with "Δ" and test specimens having less than 30% of that were marked with "x".

TABLE 1

|  | P3 | P4 | C1 | C2 | C3 |
|---|---|---|---|---|---|
| Photocurability | ○ | ○ | x | ○ | ○ |
| Out-gas measurement test | ○ (60) | ○ (60) | Δ (500) | x (1500) | ○ (60) |
| Elution amount test | ○ (800) | ○ (250) | Δ (2000) | x (5000) | x (8000) |
| Adhesion strength measurement test | ○ (20) | ○ (20) | Δ (10) | ○ (20) | ○ (20) |
| Adhesion reliability test | ○ (13) | ○ (13) | x (2) | ○ (12) | ○ (12) |

As shown in Table 1, in the photocurable resin compositions (P3 and P4) obtained in Examples 3 and 4, the curability is extremely excellent with ultraviolet light having a wavelength of 370 to 450 nm and visible light. In addition, in these compositions, the amount of out-gas components is extremely small, the elation amount of the unreacted polymerization initiator from the cured product is small and the adhesive strength is high.

In C1 obtained in Comparative Example 1, an oligomer type α-hydroxyacetophenone is used as the photopolymerization initiator, the amount of generated out-gas and the elution amount of the unreacted photopolymerization initiator are relatively small, but the photocurability is poor and adhesion strength is not exhibited. In C2 and C3 obtained in Comparative Examples 2 and 3, the photocurability is good but the amount of generation of the out-gas is large or the elution amount of the unreacted photopolymerization initiator is large.

TABLE 2

|  | P5 | P6 | C4 | C5 | C6 |
|---|---|---|---|---|---|
| Photocurability | ○ | ○ | x | ○ | ○ |
| Out-gas measurement test | ○ (60) | ○ (60) | Δ (500) | x (1500) | ○ (60) |
| Elution amount test | ○ (250) | ○ (250) | Δ (2000) | x (5000) | x (8000) |

As shown in Table 2, in the photocurable resin compositions (P5 and P6) obtained in Examples 5 and 6, the curability is extremely excellent with ultraviolet light having a wavelength of 370 to 450 nm and visible light. In addition, in these compositions, the amount of out-gas components is extremely small, the elution amount of the unreacted polymerization initiator from the cured product is small and the adhesive strength is high.

In C4 obtained in Comparative Example 4, an oligomer type α-hydroxyacetophenone is used as a photopolymerization initiator, the amount of generated out-gas and the elution amount of the unreacted photopolymerization initiator are relative small, but the photocurability is poor. In C5 and C6 obtained in Comparative Examples 5 and 6, the photocurability is good but the amount of generated out-gas is large or the elution amount of the unreacted photopolymerization initiator is large.

INDUSTRIAL APPLICABILITY

The present invention relates to a photopolymerization initiator excellent in a low out-gas property and sensitivity to ultraviolet light and visible light, and a photocurable resin composition having a low outgas property and a high adhesion strength, which may be used in the field of electronic materials and record display materials.

The present application claims priority based on Japanese Patent Application No. 2005-373642 and Japanese Patent Application No. 2005-373640 filed on Dec. 27, 2005, the disclosure of which is entirely incorporated herein as reference.

The invention claimed is:

1. A photocurable resin composition comprising a component (a) composed of an anthraquinone derivative represented by the following formula (I) and a component (b) composed of a compound having a (meth)acryloyl group in the molecule, wherein at least some of the molecules of the component (b) further have an oxiranyl group, and
the content of the component (a) is 0.01 to 10% by mass relative to the content of the component (b)

(I)

wherein X is selected from the group consisting of a phenyl group, an alkyl group having 1 to 8 carbon atoms, an alcoholic form of the phenyl group or the alkyl group, and a derivative of the alcoholic form.

2. The photocurable resin composition according to claim 1, wherein the component (a) contains a compound represented by the following formula (I')

(I')

wherein $R_1$ is selected from the group consisting of a hydrogen atom and a methyl group,
Y is selected from the group consisting of a phenylene group, its derivative, an alkylene group having 1 to 8 carbon atoms and its derivative, and
Z is selected from the group consisting of a single bond and a divalent organic group.

3. The photocurable resin composition according to claim 1, further containing 10 to 50% by mass of a component (c) composed of a compound which contains an oxiranyl group in the molecule and has no radical polymerizability, and 3 to 30% by mass of a latent epoxy curing agent (d), relative to the component (b).

4. The photocurable resin composition according to claim 3, further containing 5 to 30 parts by mass of a filler (e), relative to 100 parts by mass of the photocurable resin composition.

5. A sealing agent containing the photocurable resin composition according to claim 1.

6. A liquid crystal sealing agent containing the photocurable resin composition according to claim 1.

7. A sealing agent for a liquid crystal one drop fill process containing the photocurable resin composition according to claim 1.

8. A method of producing a liquid crystal panel, comprising; a step of applying a sealing agent on a first substrate to form a desired frame shape; a step of dropwise supplying a liquid crystal in the frame of the frame shape; a step of overlapping the first substrate and a second substrate facing to the first substrate; and a step of curing the sealing agent by light, wherein the sealing agent contains the photocurable resin composition according the claim 1.

9. The method of producing the liquid crystal panel according to claim 8, wherein further having a step of curing the sealing agent by heat.

10. The method of producing the liquid crystal panel according to claim 8, wherein the light has a wavelength of 370 nm to 450 nm.

* * * * *